(12) United States Patent
Durcan (10) Patent No.: US 9,707,381 B2
(45) Date of Patent: *Jul. 18, 2017

(54) NON-COMPLIANT MULTILAYERED BALLOON FOR A CATHETER

(71) Applicant: ABBOTT CARDIOVASCULAR SYSTEMS INC., Santa Clara, CA (US)

(72) Inventor: Jonathan P. Durcan, Temecula, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 9 days.

This patent is subject to a terminal disclaimer.

(21) Appl. No.: 14/748,376

(22) Filed: Jun. 24, 2015

(65) Prior Publication Data
US 2015/0290435 A1    Oct. 15, 2015

Related U.S. Application Data

(63) Continuation of application No. 13/775,724, filed on Feb. 25, 2013, now Pat. No. 9,095,689, which is a (Continued)

(51) Int. Cl.
*A61M 25/10* (2013.01)
*B29C 67/00* (2017.01)
(Continued)

(52) U.S. Cl.
CPC ......... *A61M 25/1029* (2013.01); *A61F 2/958* (2013.01); *A61L 29/06* (2013.01); (Continued)

(58) Field of Classification Search
CPC ............. A61M 25/10; A61M 25/1002; A61M 25/1027; A61M 25/1029; A61M 25/104; (Continued)

(56) References Cited

U.S. PATENT DOCUMENTS 4,952,357 A   8/1990  Euteneuer
5,112,304 A   5/1992  Barlow et al.
(Continued)

FOREIGN PATENT DOCUMENTS

EP    0420488    3/1991
EP    0485903    10/1996
(Continued)

OTHER PUBLICATIONS

U.S. Appl. No. 14/443,805, filed May 19, 2015.
(Continued)

*Primary Examiner* — Andrew Gilbert
(74) *Attorney, Agent, or Firm* — Baker Botts L.L.P.

(57) ABSTRACT

Balloon catheter comprises an elongate catheter shaft having a proximal section, a distal section, and an inflation lumen, and a multilayer balloon on the distal section of the shaft. The multilayer balloon comprises a first layer made of a first polymer material having a first Shore durometer hardness, a second layer made of a second polymer material having a second Shore durometer hardness lower than the first shore durometer hardness, wherein the second layer is an inner layer relative to the first layer, and an outer-most layer made of a third polymer material having a third Shore durometer hardness lower than the second Shore durometer hardness.

36 Claims, 3 Drawing Sheets

Related U.S. Application Data continuation of application No. 13/447,635, filed on Apr. 16, 2012, now Pat. No. 8,388,575, which is a continuation of application No. 12/897,202, filed on Oct. 4, 2010, now Pat. No. 8,394,055, which is a continuation of application No. 11/313,041, filed on Dec. 20, 2005, now Pat. No. 7,828,766.

(51) Int. Cl.
  *A61F 2/958* (2013.01)
  *A61L 29/06* (2006.01)

(52) U.S. Cl.
  CPC .......... *A61M 25/10* (2013.01); *A61M 25/104* (2013.01); *B29C 67/0014* (2013.01); *A61F 2250/0018* (2013.01); *A61F 2250/0063* (2013.01); *A61M 2025/1075* (2013.01); *A61M 2025/1084* (2013.01)

(58) Field of Classification Search
  CPC ... A61M 2025/1075; A61M 2025/1084; A61F 2/958; A61F 2250/0018; A61F 2250/0019; B29C 67/0014
  See application file for complete search history.

(56) References Cited

U.S. PATENT DOCUMENTS

| | | | |
|---|---|---|---|
| 5,195,969 A | 3/1993 | Wang et al. | |
| 5,207,700 A | 5/1993 | Euteneuer | |
| 5,270,086 A * | 12/1993 | Hamlin | A61L 29/041 428/35.2 |
| 5,290,306 A | 3/1994 | Trotta et al. | |
| 5,358,486 A | 10/1994 | Saab | |
| 5,447,497 A | 9/1995 | Sogard et al. | |
| 5,478,320 A | 12/1995 | Trotta | |
| 5,499,980 A | 3/1996 | Euteneuer | |
| 5,512,051 A | 4/1996 | Wang et al. | |
| 5,556,383 A | 9/1996 | Wang et al. | |
| 5,587,125 A | 12/1996 | Roychowdhury | |
| 5,613,979 A | 3/1997 | Trotta et al. | |
| 5,620,649 A | 4/1997 | Trotta | |
| 5,647,848 A | 7/1997 | Jorgensen | |
| 5,679,817 A | 10/1997 | Sakai et al. | |
| 5,755,690 A | 5/1998 | Saab | |
| 5,769,817 A | 6/1998 | Burgmeier | |
| 5,797,887 A | 8/1998 | Rosen et al. | |
| 5,807,327 A | 9/1998 | Green et al. | |
| 5,833,657 A | 11/1998 | Reinhardt et al. | |
| 5,879,369 A | 3/1999 | Ishida | |
| 5,908,406 A * | 6/1999 | Ostapchenko | A61L 29/041 428/35.7 |
| 6,004,289 A | 12/1999 | Saab | |
| 6,004,339 A | 12/1999 | Wijay | |
| 6,024,722 A | 2/2000 | Rau et al. | |
| 6,059,751 A | 5/2000 | Ostapchenko et al. | |
| 6,086,556 A | 7/2000 | Hamilton et al. | |
| 6,124,007 A * | 9/2000 | Wang | A61M 25/1029 264/512 |
| 6,132,824 A * | 10/2000 | Hamlin | A61L 29/041 428/35.2 |
| 6,136,258 A | 10/2000 | Wang et al. | |
| 6,146,356 A | 11/2000 | Wang et al. | |
| 6,171,278 B1 | 1/2001 | Wang et al. | |
| 6,242,063 B1 | 6/2001 | Ferrera et al. | |
| 6,328,925 B1 * | 12/2001 | Wang | A61M 25/1029 264/209.5 |
| 6,358,227 B1 | 3/2002 | Ferrera et al. | |
| 6,416,494 B1 * | 7/2002 | Wilkins | A61L 29/041 428/35.2 |
| 6,495,090 B1 * | 12/2002 | Wilkins | A61L 29/041 264/540 |
| 6,500,148 B1 | 12/2002 | Pinchuk et al. | |
| 6,585,688 B2 | 7/2003 | Ferrera et al. | |
| 6,620,127 B2 | 9/2003 | Lee et al. | |
| 6,620,128 B1 | 9/2003 | Simhambhatla | |
| 6,645,422 B2 | 11/2003 | Jung et al. | |
| 6,673,302 B2 | 1/2004 | Wang et al. | |
| 6,695,809 B1 * | 2/2004 | Lee | A61F 2/958 604/96.01 |
| 6,756,094 B1 | 6/2004 | Wang et al. | |
| 6,796,960 B2 | 9/2004 | Cioanta et al. | |
| 6,835,189 B2 | 12/2004 | Musbach et al. | |
| 6,866,650 B2 | 3/2005 | Stevens et al. | |
| 6,875,197 B1 | 4/2005 | Simhambhatla et al. | |
| 6,896,842 B1 | 5/2005 | Hamilton et al. | |
| 6,911,038 B2 | 6/2005 | Mertens et al. | |
| 6,946,092 B1 | 9/2005 | Bertolino et al. | |
| 6,949,112 B1 * | 9/2005 | Sridharan | A61L 29/06 606/194 |
| 6,951,675 B2 | 10/2005 | Chin et al. | |
| 7,026,026 B2 | 4/2006 | Ferrera et al. | |
| 7,029,732 B2 | 4/2006 | Wang et al. | |
| 7,074,206 B2 * | 7/2006 | Lee | A61L 29/049 428/36.9 |
| 7,112,357 B2 | 9/2006 | Miller et al. | |
| 7,147,817 B1 * | 12/2006 | Lim | A61M 25/1006 264/289.6 |
| 7,195,638 B1 | 3/2007 | Sridharan | |
| 7,335,185 B2 | 2/2008 | Tang et al. | |
| 7,781,038 B2 | 8/2010 | Hamilton et al. | |
| 7,815,628 B2 | 10/2010 | Devens, Jr. | |
| 7,828,766 B2 * | 11/2010 | Durcan | A61F 2/958 604/103.06 |
| 7,906,066 B2 | 3/2011 | Wilson et al. | |
| 7,942,847 B2 * | 5/2011 | Stupecky | A61M 25/10 604/103.06 |
| 8,211,392 B2 * | 7/2012 | Grubert | B01D 53/944 423/213.2 |
| 8,388,575 B2 * | 3/2013 | Durcan | A61F 2/958 604/103.06 |
| 8,394,055 B2 * | 3/2013 | Durcan | A61F 2/958 604/103.06 |
| 8,535,596 B2 * | 9/2013 | Durcan | A61F 2/958 264/512 |
| 8,568,648 B2 * | 10/2013 | Stupecky | A61M 25/10 264/512 |
| 8,703,260 B2 * | 4/2014 | Simpson | A61F 2/958 264/234 |
| 9,095,689 B2 * | 8/2015 | Durcan | A61F 2/958 |
| 9,132,259 B2 * | 9/2015 | Lin | A61M 25/1029 |
| 9,180,620 B2 * | 11/2015 | Devens, Jr. | A61M 25/1002 |
| 2002/0018866 A1 * | 2/2002 | Lee | A61L 29/06 428/36.8 |
| 2002/0087165 A1 | 7/2002 | Lee et al. | |
| 2002/0118866 A1 * | 8/2002 | Breeuwer | G06T 7/62 382/128 |
| 2002/0165523 A1 * | 11/2002 | Chin | A61M 25/1029 604/523 |
| 2002/0171180 A1 | 11/2002 | Simhambhatla | |
| 2004/0096606 A1 * | 5/2004 | Lee | A61L 29/049 428/35.2 |
| 2004/0170782 A1 | 9/2004 | Wang et al. | |
| 2004/0173935 A1 | 9/2004 | Lim et al. | |
| 2004/0191443 A1 | 9/2004 | Hamlin | |
| 2005/0043679 A1 | 2/2005 | Devens et al. | |
| 2005/0124976 A1 | 6/2005 | Devens et al. | |
| 2005/0124978 A1 | 6/2005 | Kim | |
| 2005/0186370 A1 * | 8/2005 | Hamilton | A61L 29/049 428/35.2 |
| 2005/0228429 A1 | 10/2005 | Burgmeier et al. | |
| 2005/0238833 A1 * | 10/2005 | Wang | A61M 25/1029 428/36.91 |
| 2005/0277878 A1 | 12/2005 | Lee | |
| 2006/0165926 A1 | 7/2006 | Weber | |
| 2007/0060863 A1 * | 3/2007 | Goeken | A61B 17/320725 604/22 |
| 2007/0142771 A1 | 6/2007 | Durcan | |
| 2007/0142772 A1 * | 6/2007 | Deshmukh | A61L 29/06 604/103.06 |
| 2007/0167973 A1 | 7/2007 | Stupecky et al. | |

(56) References Cited

U.S. PATENT DOCUMENTS

| | | | |
|---|---|---|---|
| 2007/0250101 | A1 | 10/2007 | Horn et al. |
| 2008/0045928 | A1 | 2/2008 | Simpson et al. |
| 2008/0065188 | A1 | 3/2008 | Pallazza |
| 2009/0156998 | A1 | 6/2009 | Arana et al. |
| 2010/0010470 | A1 | 1/2010 | Bates |
| 2011/0022150 | A1 | 1/2011 | Durcan et al. |
| 2012/0065718 | A1 | 3/2012 | Simpson et al. |
| 2012/0145317 | A1 | 6/2012 | Durcan et al. |
| 2012/0203324 | A1 | 8/2012 | Durcan |
| 2013/0172817 | A1 | 7/2013 | Durcan et al. |
| 2014/0142505 | A1 | 5/2014 | Lin et al. |
| 2014/0190630 | A1 | 7/2014 | Simpson et al. |

FOREIGN PATENT DOCUMENTS

| | | |
|---|---|---|
| EP | 0611576 | 1/1997 |
| EP | 0592885 | 7/2009 |
| JP | H05-305146 | 11/1993 |
| JP | H06-507101 | 8/1994 |
| JP | 2001/029450 | 2/2001 |
| JP | 2005-167638 | 6/2005 |
| JP | 2007/000157 | 1/2007 |
| WO | WO 92/08512 | 5/1992 |
| WO | WO 95/18647 | 7/1995 |
| WO | WO 01/51115 | 7/2001 |
| WO | WO 02/056930 | 7/2002 |
| WO | WO 2005/021083 | 3/2005 |
| WO | WO 2005/065735 | 7/2005 |
| WO | WO 2006/126311 | 11/2006 |

OTHER PUBLICATIONS

U.S. Appl. No. 14/820,664, filed Aug. 7, 2015.
U.S. Appl. No. 11/313,041, Oct. 4, 2010 Issue Fee payment.
U.S. Appl. No. 11/313,041, Jul. 2, 2010 Notice of Allowance.
U.S. Appl. No. 11/313,041, Jun. 4, 2010 Request for Continued Examination (RCE).
U.S. Appl. No. 11/313,041, Apr. 6, 2010 Notice of Allowance.
U.S. Appl. No. 11/313,041, Mar. 1, 2010 Amendment and Request for Continued Examination (RCE).
U.S. Appl. No. 11/313,041, Oct. 27, 2009 Final Office Action.
U.S. Appl. No. 11/313,041, Jun. 22, 2009 Response to Non-Final Office Action.
U.S. Appl. No. 11/313,041, Apr. 17, 2009 Examiner Interview Summary.
U.S. Appl. No. 11/313,041, Jan. 22, 2009 Non-Final Office Action.
U.S. Appl. No. 11/313,041, Dec. 8, 2008 Amendment and Request for Continued Examination (RCE).
U.S. Appl. No. 11/313,041, Sep. 16, 2008 Final Office Action.
U.S. Appl. No. 11/313,041, May 12, 2008 Response to Non-Final Office Action.
U.S. Appl. No. 11/313,041, Feb. 21, 2008 Non-Final Office Action.
U.S. Appl. No. 12/897,202, Feb. 7, 2013 Issue Fee payment.
U.S. Appl. No. 12/897,202, Nov. 7, 2012 Notice of Allowance.
U.S. Appl. No. 13/397,140, Aug. 16, 2013 Issue Fee Payment.
U.S. Appl. No. 13/397,140, May 17, 2013 Notice of Allowance.
U.S. Appl. No. 13/397,140, Feb. 26, 2013 Response to Non-Final Office Action.
U.S. Appl. No. 13/397,140, Oct. 26, 2012 Non-Final Office Action.
U.S. Appl. No. 13/447,635, Feb. 5, 2013 Issue Fee payment.
U.S. Appl. No. 13/447,635, Nov. 5, 2012 Notice of Allowance.
U.S. Appl. No. 12/881,733, Mar. 4, 2014 Issue Fee Payment.
U.S. Appl. No. 12/881,733, Dec. 4, 2013 Notice of Allowance.
U.S. Appl. No. 12/881,733, Feb. 12, 2013 Restriction Requirement.
U.S. Appl. No. 12/881,733, Mar. 12, 2013 Response to Restriction Requirement.
U.S. Appl. No. 12/881,733, May 30, 2013 Non-Final Office Action.
U.S. Appl. No. 12/881,733, Oct. 30, 2013 Response to Non-Final Office Action.
U.S. Appl. No. 12/881,733, Oct. 11, 2013 Applicant-Initiated Interview Summary.
U.S. Appl. No. 12/881,733, Sep. 24, 2013 Applicant-Initiated Interview Summary.
U.S. Appl. No. 13/680,299, Aug. 7, 2015 Issue Fee Payment.
U.S. Appl. No. 13/680,299, May 8, 2015 Notice of Allowance.
U.S. Appl. No. 13/680,299, Feb. 24, 2015 Response to Non-Final Office Action.
U.S. Appl. No. 13/680,299, Nov. 26, 2014 Non-Final Office Action.
U.S. Appl. No. 13/680,299, Nov. 10, 2014 Response to Restriction Requirement.
U.S. Appl. No. 13/680,299, Sep. 8, 2014 Restriction Requirement.
U.S. Appl. No. 13/775,724, Nov. 20, 2014 Non-Final Office Action.
U.S. Appl. No. 13/775,724, Feb. 20, 2015 Response to Non-Final Office Action.
U.S. Appl. No. 13/775,724, Feb. 26, 2015 Applicant Initiated Interview Summary.
U.S. Appl. No. 13/775,724, Mar. 24, 2015 Notice of Allowance.
U.S. Appl. No. 13/775,724, Jun. 24, 2015 Issue Fee Payment.
U.S. Appl. No. 13/775,752, Aug. 5, 2015 Notice of Allowance.
U.S. Appl. No. 14/204,885, Oct. 6, 2015 Non-Final Office Action.
("Hytrel" data sheet) including Hytrel TPC-ET, (94 pages), date not available.
"CLEARTUF 8006", Shell Chemical Company. date not available.
"Comparison of Arnitel El 740 With Hytrel 7246", retrieved from co-pending U.S. Appl. No. 11/313,041 on Apr. 1, 2013.
Affidavit of Dr. John Chen regarding the measurements for Traytuf 7357 mentioned in Material Testing analysis & Characterization of Traytuf 7357. 2009 (month and date are not available).
Ahearne, et al., "Mechanical characterisation of hydrogels for tissue engineering applications," Topics in Tissue Engineering, 4 (Chapter 12): 3-16, 2008 (month and date are not available).
Concise Encyclopedia of Polymer Science and Engineering, p. 759, 815, 1990 (month and date are not available).
Data sheet Aurum PL450C (2 sheets), received Oct. 19, 2009.
Data Sheets of Hytrel grades (2 pages), date not available.
DuPont Engineering Polymers, "From concept to commercialisation," (40 pages) Sep. 1996 (date is not available).
DuPont Product and Properties Guide, "Hytrel polyester elastomer" Nov. 1999 (date is not available).
DuPont Product Information, "Hytrel polyester elastomer", Nov. 1993 (date is not available).
DuPont Product Information, Injection Molding Guide, "Hytrel polyester elastomer", Oct. 1996 (date is not available).
Extract from Wikipedia, "Polyimide" (2 sheets) 2009 (month and date are not available).
Mat Web Information for Plexar (25 pages) Accessed Oct. 20, 2008.
Material Testing Analysis & Characterization of Traytuf 7357 (5 pages) 2007 (month and date are not available).
Nylon Plastics Handbook, Melvin I. Kohan 1995, pp. 298-302 (month and date are not available).
Oudshoorn et al., "Synthesis and characterization of hyperbranched polyglycerol hydrogels," Biomaterials, 27:5471-5479, Jul. 2006.
Table "Hytrel grades available before Oct. 1996" (date is not available).
Technical data sheet "SELAR PT 4368" Oct. 31, 1990.
Technical data sheet "TRAYTUF® 7357 Polyester Resin", date not available.
Thesis for the Degree of Master of Science by Samantha Garramone, (65 pages) 2001 (month and date are not available).

\* cited by examiner

NON-COMPLIANT MULTILAYERED BALLOON FOR A CATHETER

RELATED APPLICATIONS

This application is a continuation of U.S. application Ser. No. 13/775,724, filed Feb. 25, 2013 (issued as U.S. Pat. No. 9,095,689 on Aug. 4, 2015), which is a continuation of U.S. application Ser. No. 13/447,635, filed Apr. 16, 2012 (issued as U.S. Pat. No. 8,388,575 on Mar. 5, 2013), which is a continuation of U.S. application Ser. No. 12/897,202, filed Oct. 4, 2010 (issued as U.S. Pat. No. 8,394,055 on Mar. 12, 2013), which is a continuation of U.S. application Ser. No. 11/313,041, filed Dec. 20, 2005 (issued as U.S. Pat. No. 7,828,766 on Nov. 9, 2010), the contents of each of which is incorporated herein by reference in its entirety.

BACKGROUND OF THE INVENTION

The invention relates to the field of intravascular medical devices, and more particularly to a balloon for a catheter.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

Catheter balloons are typically manufactured independently of the catheter shaft and then secured to the catheter shaft with an adhesive or other bonding method. In standard balloon manufacture, a polymer tube is blown biaxially under the action of axial tension, internal pressure, and heat within a mold. The polymer tube may either be simultaneously stretched in the radial and axial directions, or sequentially, by first stretching axially and then radially. The starting dimensions of the polymer tube and the finished dimensions of the blow-molded balloon within the mold are a measure of the degree to which the polymeric material has been stretched and oriented during balloon blowing, and affect important characteristics of the finished balloon such as rupture pressure and compliance. The blow-up-ratio (BUR), namely, the ratio of the outer diameter of the blown balloon (i.e., the mold inner diameter) to the inner diameter of the polymer tube, is a measure of those dimensions. Beyond a critical BUR for a given polymer, the balloon blowing process becomes unstable and the polymer tubing often ruptures or tears before a balloon is fully formed.

In the standard blow molding process, an initiated bubble rapidly grows in diameter until it is constrained by the mold wall. The hoop stress in the wall of the tubing, as it grows into a balloon, may be approximated by the expression:

$$\sigma_h = (P \cdot R)/\delta$$

where P is the inflation pressure, R is the mean radius of the polymeric tube at any time during the inflation and $\delta$, delta, is the wall thickness of the tubing. For a balloon to be initiated from the tubing, the inflation pressure should be such that the wall hoop stress exceeds the material resistance (typically the yield stress) to stretching at the blowing temperature. Once a balloon is initiated from the tubing, it grows rapidly in size until it touches the mold wall. As the balloon grows, the radius increases and the balloon wall thickness decreases. This results in a rapid increase in the wall hoop stress during constant pressure blowing. If the wall hoop stress of the growing balloon exceeds the ultimate hoop strength of the material, rupture will occur. As a result, there is a limit to the BUR (i.e., a maximum attainable BUR) of a polymeric material forming the balloon layer(s).

In the design of catheter balloons, balloon characteristics such as strength, flexibility and compliance must be tailored to provide optimal performance for a particular application. Angioplasty and stent delivery balloons preferably have high strength for inflation at relatively high pressure, and high flexibility and softness for improved ability to track the tortuous anatomy and cross lesions. The balloon compliance, which depends on factors such as the nature of the balloon material, the balloon wall thickness, and processing conditions, is chosen so that the balloon will have a desired amount of expansion during inflation. Compliant balloons, for example balloons made from materials such as polyethylene, exhibit substantial stretching upon the application of tensile force. Noncompliant balloons, for example balloons made from materials such as PET, exhibit relatively little stretching during inflation, and therefore provide controlled radial growth in response to an increase in inflation pressure within the working pressure range. However, noncompliant balloons generally have relatively low flexibility and softness, so that it has been difficult to provide a low compliant balloon with high flexibility and softness for enhanced catheter trackability. A balance is typically struck between the competing considerations of softness/flexibility and noncompliance, which, as a result, has limited the degree to which the compliance of catheter balloons can be further lowered.

Therefore, what has been needed is a catheter balloon with very low compliance, yet with excellent ability to track within the patient's vasculature and cross lesions therein. The present invention satisfies these and other needs.

SUMMARY OF THE INVENTION

The invention is directed to a balloon catheter having a multilayered balloon which has a first layer and at least a second layer, and which has noncompliant limited radial expansion beyond the nominal diameter of the balloon. By selecting the polymeric materials forming the balloon layers, and arranging and radially expanding the multiple layers of the balloon in accordance with the invention, a balloon is provided having an improved low compliance, preferably in combination with high flexibility and softness.

A multilayered balloon of the invention is preferably formed in whole or in part of coextruded polymeric tubular layers, and provides for ease of manufacture of the balloon and balloon catheter formed therefrom. The multilayered balloon is typically formed by conventional blow-molding in which a multilayered polymeric tube is radially expanded within a balloon mold. The resulting multilayered balloon has an inflated shape which corresponds to the inner surface of the mold and which has a diameter about equal to the inner diameter of the balloon mold, commonly referred to as the balloon's nominal working diameter. The nominal pressure is the inflation pressure required to fill the balloon to the nominal working diameter. In accordance with the invention, the balloon expands a very small amount (i.e., noncompliantly) at pressures above the nominal pressure. As a result, the balloon minimizes injury to a patient's blood vessel, which can otherwise occur if the balloon continues to expand a substantial uncontrolled amount at increasing inflation pressures above nominal.

As discussed above, the blow-up-ratio (BUR) of the balloon formed from a polymer tube should be understood to refer to the ratio of the outer diameter of the blown balloon expanded within the mold (i.e., the mold inner diameter) to the inner diameter of the polymer tube prior to being expanded in the mold. Each individual layer of the multilayered balloon similarly has its own BUR based on the ratio of the inner diameter of the mold and the inner diameter (prior to expansion in the mold) of the layer of the polymeric tube. For a given balloon wall thickness, the rupture strength generally increases and the radial compliance decreases as the balloon BUR increases. For standard pressure driven blow molding of catheter balloons, typical BURs range from about 4.5 to about 8.0 depending on the material and the product application.

A method of making a balloon of the invention increases the amount of balloon material that is highly oriented in the radial direction, to provide a balloon with limited radial expansion at increasing inflation pressures (i.e., to provide a noncompliant balloon). Specifically, a multilayered balloon of the invention has polymeric materials that can be expanded to higher BURs as the inner layer(s) of the balloon, while lower BUR materials are the outer layer(s) of the balloon. In a presently preferred embodiment, the balloon has a first layer of a first polymeric material and a second layer of a second polymeric material which has a lower Shore durometer hardness than the first polymeric material and which can be expanded during balloon blowing to a higher BUR (without rupturing or tearing) than the higher Shore durometer hardness material of the first layer, and the second layer is an inner layer relative to the first layer. For example, one embodiment, the multilayered balloon inner layer is formed of a polyether block amide (PEBA) material (e.g., commercially available as PEBAX®) having a Shore durometer hardness of about 60-70 D while the outer layer is formed of a PEBA material having a higher Shore durometer hardness of about 70-72 D. However, a variety of suitable materials can be used including materials which are of the same material classification/family, or different classes of materials. The multilayered balloon generally has two or more layers (i.e., layers formed of materials which differ in some respect such as different Shore durometer hardnesses), although it typically does not have more than five layers.

Despite presence of the lower durometer material forming the second (inner) layer of the multilayered balloon, a first embodiment of the invention provides a balloon which has a very low compliance. For example, a balloon of the invention having a first (outer) layer of a first durometer, and one or more inner layer(s) of successively lower durometers (i.e., increasingly softer materials), has a lower compliance than a balloon having about the same wall thickness but formed of 100% of the highest durometer material (i.e., the material forming the outer-most layer of the balloon of the invention). Compared to a balloon formed of 100% of the highest durometer material, a balloon of the invention has effectively replaced a part of the balloon wall thickness with the layer(s) of lower durometer (softer) material(s), which would typically be expected to increase the compliance. While not wishing to be bound by theory, it is believed that the balloon provides the noncompliant behavior through the specific combination of highly oriented layers of the balloon, and particularly by maximizing the orientation of the inner layer(s) of the balloon. The inner layer orientation significantly affects compliance of the balloon. By selecting and arranging different materials that can be blown to different BURs in accordance with the invention, the balloon has layers with successively increasing BURs from the outer to the inner layer(s), such that the BUR of each layer is preferably maximized and the inner layer(s) have particularly high BURs. The layers of the balloon are therefore optimized for compliance purposes. Although additional layers may be added to the balloon, to, for example, increase the total wall thickness to a desired value, the arrangement of the basic layers in accordance with the invention cannot be varied without resulting in a higher compliance balloon.

Additionally, the invention can alternatively provide for a balloon with a low compliance but with very thin walls. For example, one embodiment is directed to a multilayered balloon having a first (outer) layer of a first durometer material and one or more inner layer(s) of successively lower durometer materials which has a compliance not substantially greater than (e.g., not more than about 10% to about 20% greater than), and preferably about equal to a balloon which is formed of 100% of the highest durometer material but which has a larger wall thickness than the multilayered balloon of the invention. The embodiment of the balloon having a very thin total wall thickness provides an improved low profile and flexibility due to the thinner walls of the balloon, but, in accordance with the invention, nonetheless continues to provide a low compliance despite the thin wall.

The rupture pressure and compliance of a balloon are affected by the strength (e.g., hoop strength) of a balloon. Because a softer material generally has a relatively lower hoop strength, the presence of the lower durometer material forming the inner layer(s) of the balloon is not generally expected to provide a relatively higher modulus balloon. However, a multilayered balloon of the invention preferably has a higher modulus than, and a rupture pressure which is not substantially less than, a balloon formed of 100% of the highest durometer material.

The presence of the lower durometer material inner layer(s) does provide layers of increased softness, and therefore preferably provides a balloon that is softer and more flexible than a balloon formed of 100% of the highest durometer material.

Prior multilayered balloons with layers of polymers having different strengths/softnesses typically arrange the layers so that the durometer hardnesses decreased from the inner to the outer layer, for various balloon design considerations. For example, lower durometer (softer) materials are typically preferred as outer layers for design considerations such as pinhole resistance, stent retention, and the like. In contrast, a balloon of the invention arranges layers so that the highest durometer material has on an inner surface thereof a layer of a lower durometer material, and configures the layers to provide for a maximized BUR which produces an improved combination of characteristics including a very low compliance. However, with the inner layer(s) of the balloon of the invention optimized for compliance purposes as discussed above, one embodiment of a balloon of the invention has an outer-most layer of a relatively soft material, to, for example, enhance stent retention.

The compliance of the balloon should be understood to refer to the degree to which the polymeric wall of the balloon stretches/distends as the balloon expands beyond the nominal diameter of the balloon. The compliance curve expresses the balloon outer diameter as a function of increasing inflation pressure in millimeters/atmospheres (mm/atm), so that a steeper curve or section of the curve indicates a higher compliance than a flatter curve. The term "noncompliant", should be understood to mean a balloon with compliance of not greater than about 0.03 mm/atm, preferably not greater than about 0.025 mm/atm. In contrast, compliant balloons typically have a compliance of greater than about 0.045 mm/atm. A noncompliant balloon of the invention generally has a compliance above nominal of about 0.01 to about 0.02 mm/atm, for a 3.0 mm diameter balloon. The compliance of the balloon is typically about 25% to about 50% less than the compliance of a balloon with a similar wall thickness but made from 100% of the first (e.g., highest durometer) material.

In a presently preferred embodiment, the polymeric material of the first layer and the polymeric material of the second layer of the multilayered balloon are elastomers, which typically have a lower flexural modulus than nonelastomers. Elastomeric polymers suitable for forming the first and/or second layer of the multilayered balloon typically have a flexural modulus of about 40 kpsi to about 110 kpsi. Thus, unlike nonelastomeric materials such as PET which have been used in the past to provide relatively low compliance catheter balloons, the multilayered noncompliant balloon of the invention is preferably formed of one or more elastomers which provide for improved balloon flexibility.

One aspect of the invention is directed to a method of making a noncompliant multilayered balloon for catheter. The method generally comprises selecting a first and a second polymeric material, the second polymeric material having been determined to have a higher maximum attainable BUR than the first polymeric material, and forming a multilayered tube having a first layer of the first polymeric material, and a second layer of the second polymeric material wherein the second layer is an inner layer relative to the first layer. The maximum attainable BUR of a polymeric material is typically determined experimentally, although characteristics such as the ultimate tensile strength and elongation to break of the material maybe indicative at least for some materials (e.g., a material having a relatively higher ultimate tensile strength and elongation to break is expected, in general, to have a higher maximum BUR). The inner diameter of each layer of the multilayered tube is selected so that the ratio of the inner diameter of the balloon mold and the inner diameter of the layer of the multilayered tube (prior to being radially expanded in the balloon mold) is substantially at a maximum blow-up-ratio for the polymeric material forming the layer. Thus, the method includes forming the blow-molded multilayered balloon by radially expanding the multilayered tube in a mold, so that radially expanding the tube to the mold inner diameter radially expands each layer substantially to the maximum blow-up-ratio of the polymeric material forming the layer, such that the multilayered balloon has a lower compliance above the nominal working diameter than a balloon consisting of the first elastomeric polymeric material.

Various designs for balloon catheters well known in the art may be used in the catheter system of the invention. For example, conventional over-the-wire balloon catheters for angioplasty or stent delivery usually include a guidewire receiving lumen extending the length of the catheter shaft from a guidewire proximal port in the proximal end of the shaft to a guidewire distal port in the catheter distal end. Rapid exchange balloon catheters for similar procedures generally include a relatively short guidewire lumen extending from a guidewire port located distal to the proximal end of the shaft to the catheter distal end.

The multilayered balloon of the invention provides a very low compliance for controlled balloon expansion, without compromising relatively high flexibility and softness for excellent ability to track the patient's vasculature and cross lesions. As a result, the method of the invention has improved performance due to the flexibility, softness, and controlled expansion of the balloon. The balloon provides the surprising result of a very low compliance from the addition of the lower durometer (softer) second material. Consequently, a multilayered balloon of the invention will provide a much lower compliance than a balloon with the same wall thickness but made from just the higher durometer (stiffer) material, or will provide a much thinner walled balloon but without the expected increase in compliance. These and other advantages of the invention will become more apparent from the following detailed description of the invention and the accompanying exemplary drawings.

DETAILED DESCRIPTION OF THE PREFERRED EMBODIMENTS

Figure 1:
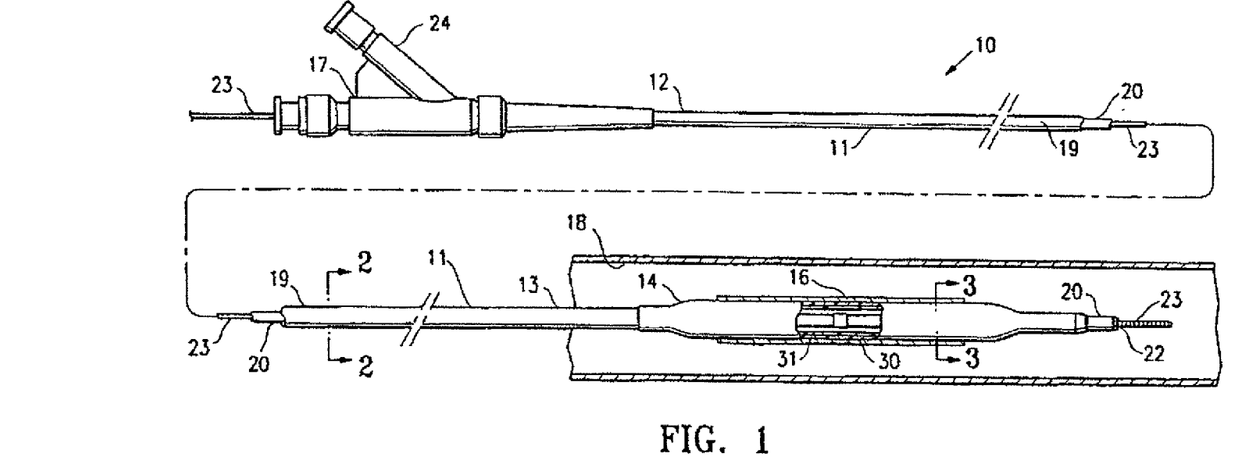
FIG. 1 is an elevational view, partially in section, of an over-the-wire type stent delivery balloon catheter embodying features of the invention.
Figure 4:
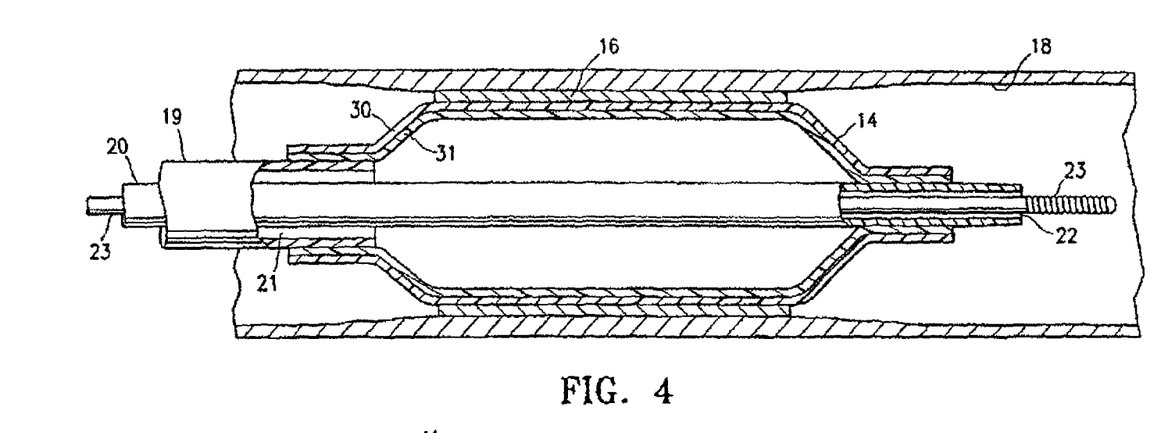
FIG. 4 illustrates the method of FIG. 1 with the balloon inflated.

FIG. 1 illustrates a stent delivery balloon catheter 10 which embodies features of the invention, generally comprising an elongated catheter shaft 11 having a proximal shaft section 12, a distal shaft section 13, an inflation lumen 21, and a guidewire lumen 22 configured to slidably receive a guidewire 23 therein, and having a balloon 14 mounted on the distal shaft section. An adapter 17 on a proximal end of the catheter shaft provides access to the guidewire lumen 22, and has an arm 24 configured for connecting to a source of inflation fluid (not shown). FIG. 1 illustrates the balloon in a noninflated configuration for advancement within a patient's body lumen 18. A radially expandable stent 16 is releasably mounted on the balloon 14 for delivery and deployment within the body lumen 18. The balloon catheter 10 is advanced in the body lumen 18 with the balloon 14 in the noninflated configuration, and the balloon inflated by introducing inflation fluid into the balloon interior to expand the balloon 14 and stent 16 mounted thereon. FIG. 4 illustrates the balloon catheter 10 with the balloon in the inflated configuration to expand the stent against the wall of the body lumen 18. The balloon 14 is then deflated to allow for repositioning or removal of the catheter from the body lumen 18, leaving the stent 16 implanted in the body lumen 18.

Figure 2:
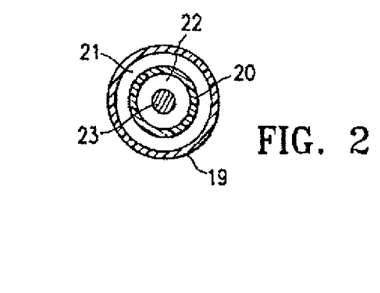
FIGS. 2 and 3 are transverse cross sectional views of the catheter of FIG. 1, taken along lines 2-2 and 3-3, respectively.
Figure 3:
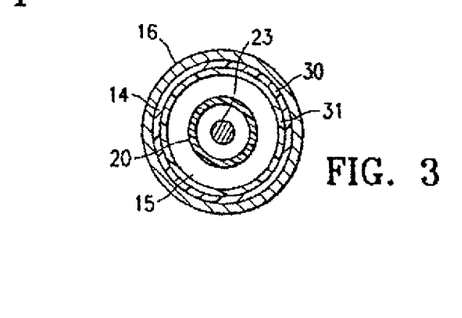

In the illustrated embodiment, the shaft comprises an outer tubular member 19 defining the inflation lumen 21, and an inner tubular member 20 defining the guidewire lumen 22 and positioned in the outer tubular member 19 such that the inflation lumen 21 is the annular space between the inner surface of the outer tubular member 19 and the outer surface of the inner tubular member 20, as best shown in FIG. 2 illustrating a transverse cross section of the catheter of FIG. 1, taken along line 2-2. The balloon 14 has a proximal skirt section sealingly secured to the distal end of the outer tubular member 19, and a distal skirt section sealingly secured to a distal end of the inner tubular member 20, so that an interior 15 of the balloon is in fluid communication with the inflation lumen 21 of the shaft. FIG. 3 illustrates a transverse cross section of the catheter of FIG. 1, taken along line 3-3, although the space between the inner surface of the noninflated balloon and the outer surface of the portion of the shaft 11 therein is somewhat exaggerated in FIGS. 1 and 3, for ease of illustration. A variety of alternative suitable catheter shaft configurations can be used as are conventionally known.

Although not illustrated, the balloon 14 of the invention typically has a noninflated configuration with wings wrapped around the balloon to form a low profile configuration for introduction and advancement within a patient's body lumen. As a result, the balloon inflates to a nominal working diameter by unfolding and filling the molded volume of the balloon.

Balloon 14 has a first layer 30, and a second layer 31 which is an inner layer relative to the first layer 30. In the illustrated embodiment, the second layer 31 is on an inner surface of the first layer 30, with the first layer 30 defining an outer surface of the balloon 14 and the second layer 31 defining an inner surface of the balloon 14. However, the balloon 14 of the invention can alternatively have one or more additional layers (not shown). Additional layer(s) increase the dimensions of the tube/balloon formed therefrom to a desired value, and/or can be used to provide an inner or outer surface of the balloon with a desired characteristic. Therefore, it should be understood that the balloon 14 of the invention discussed below has at least two layers, and optionally includes one or more additional layers, unless otherwise noted as having a specified set number of layers.

The first (outer) layer 30 is formed of a first polymeric material, and the second (inner) layer 31 is formed of a second polymeric material that can be expanded to a higher BUR than the first polymeric material. The second (inner) layer 31 is at a BUR which is typically about 15% to about 40% greater than the BUR of the first (outer) layer 30. Each layer 30, 31 is preferably at its maximum BUR, so that the balloon has layers of highly oriented material and, consequently, a very low compliance.

A variety of suitable materials can be used to form the first and second layers 30, 31, including polyamides, polyurethanes, and polyesters. In a presently preferred embodiment, the first and second polymeric materials are elastomers providing a relatively low flexural modulus for balloon flexibility, although nonelastomers can alternatively be used. Presently preferred materials are from the same polymeric family/class such as polyamides including nylons and polyether block amides (PEBAX). Forming the layers of compatible polymeric materials allows for heat fusion bonding the layers together. The layers can alternatively be formed of different polymer classes which are not sufficiently compatible to fusion bond together, in which case a tie layer is typically provided between the outer and inner layers 30, 31 to bond the balloon layers together. For example, a PET inner layer and a PEBAX typically have a tie layer of an adhesive polymer such as Primacor (a functionalized polyolefin) therebetween.

The balloon 14 is formed by a method in which the layers of material that can be expanded to higher BURs are the inner layers of the balloon tubing, and lower BUR materials are the outer layers, and the balloon is blow-molded such that each layer is optimized for radial orientation. The resulting balloon has an increased resistance to radial expansion at increasing inflation pressures.

The balloon 14 is blow-molded from a multilayered tube which has the first layer 30, and the second layer 31 as an inner layer relative to the first layer 30. However, as discussed above, a balloon of the invention may have one or more additional layers, so that the tubing used to blow-mold the balloon would similarly be formed with the additional layer(s). The tube is typically formed by coextrusion, although a variety of suitable method may be used. For example, in one embodiment, a multilayered tube is formed by coextruding at least two layers, and one or more additional layers are added to the coextruded tube for example by heat shrinking, dip coating, adhesive or fusion bonding, or frictionally engaging the additional layer(s) to the coextruded tube.

Figure 5:
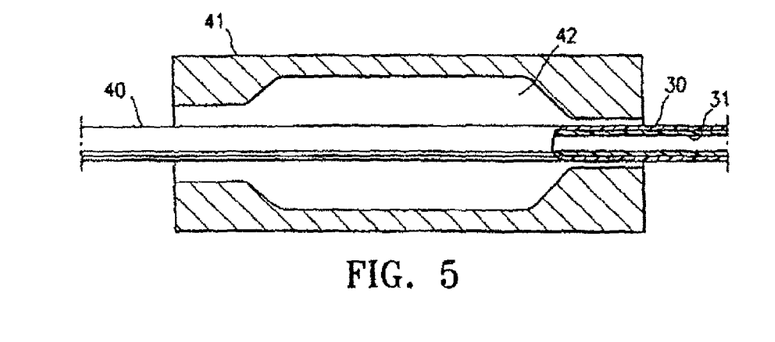
FIG. 5 is a longitudinal cross sectional view of multilayered balloon tubing in a balloon mold prior to being radially expanded therein, in a method embodying features of the invention.

The multilayered tube is then radially expanded in a balloon mold to form the balloon 14. FIG. 5 illustrates the multilayered tube 40 in a balloon mold 41 having an interior chamber 42 with a shape configured to form the balloon 14, and an inner diameter about equal to the nominal working diameter of the expanded balloon 14. The multilayered tube 40 is typically stretched axially and heated during blow molding in the balloon mold, as is conventionally known. For example, in one embodiment, the tube is longitudinally stretched by about 200% during blow molding, which produces a biaxially oriented balloon. The single wall thickness of the tube (prior to being radially expanded in the mold) is about 0.1 to about 0.4 min, and the single wall thickness of the resulting balloon (radially expanded in the mold) is about 0.01 to about 0.04 mm, depending on the desired balloon characteristics and uses.

The materials and dimensions of the multilayered tube 40 and balloon mold 41 are selected so that each layer of the resulting balloon has been radially expanded to substantially its maximum possible amount, expressed as the BUR of the balloon layers. In a presently preferred embodiment, the outer layer 30 has a higher Shore durometer hardness and therefore lower elongation than the one or more inner layers. The elongation of each layer is typically about 10% to about 50%, and more specifically about 20% more than the elongation of the outer layer immediately adjacent thereto.

In a presently preferred embodiment, the first (outer) layer 30 is a PEBAX having a Shore durometer hardness of about 72 D, and the second (inner) layer 31 is a PEBAX having a Shore durometer hardness of about 63 D. The PEBAX 72 D outer layer 30 typically has a BUR of between about 6 and 7, and the PEBAX 63 D inner layer 31 a BUR of between about 7 and 8.

In one embodiment, a mid layer (not shown) of intermediate BUR and/or durometer hardness is provided between the outer and inner layers 30, 31. For example, in one presently preferred embodiment, the balloon 14 has a first, outer layer 30 of PEBAX 72 D, a second, inner layer 31 of PEBAX 63 D, and a midlayer (not shown) therebetween of PEBAX 70 D. In a presently preferred embodiment, the inner and mid layers have a smaller wall thickness than the highest durometer layer therearound, and typically together make up about 5% to about 15% of the total wall thickness of the multilayered balloon. The balloon 14 can similarly have one or more additional layers (not shown) which similarly continue the pattern of sequentially increasing BUR and/or durometer from the inner toward the outer layers of the balloon. However, in one embodiment, the balloon 14 has a relatively soft outer-most layer (not shown) having a Shore durometer hardness less than the immediately adjacent inner layer of the balloon, which facilitates embedding the stent 16 into the outer surface of the balloon for improved stent retention. Such a relatively soft outer-most layer typically has of a relatively low Shore durometer hardness of about 40 D to about 55 D.

The multilayered balloon of the invention has a low compliance, and a relatively high rupture pressure, particularly when compared to a balloon of otherwise similar construction but formed solely of the highest durometer material used to make the multilayered balloon of the invention (e.g., a 72 D PEBAX outer layer of multilayered balloon 14), or compared to a balloon formed of layers of different durometer materials but not layered in accordance with the invention. The compliance is typically determined for the pressure range extending from the nominal pressure (i.e., the pressure required to fill the molded volume of the balloon to the blow-molded nominal diameter) to the burst pressure or the rated burst pressure of the balloon. The rated burst pressure (RBP), calculated from the average rupture pressure, is the pressure at which 99.9% of the balloons can be pressurized to without rupturing, with 95% confidence.

The multilayered balloon 14 has a nominal pressure of about 6 to about 12 atm, and more typically of about 7 to about 9 atm, and a RBP of about 14 to about 22 atms, more typically about 18 to about 20 atms. The rupture pressure is typically about equal to, greater than, or not substantially less than (i.e., not more than about 5% to about 15% less than) a rupture pressure of a balloon of otherwise similar construction but formed solely of the highest durometer material.

In one embodiment, a multilayered balloon of the invention having at least a 72 D PEBAX outer layer and a 63 D PEBAX inner layer reaches the nominal diameter of the balloon at about 8 to about 9 atm, and thereafter stretches in a noncompliant manner with a compliance of about 0.01 to about 0.02 mm/atm within the working pressure range (e.g., 8-20 atm) of the multilayered balloon to a diameter which is not more than about 8% greater than the nominal diameter.

Due to the presence of the softer durometer inner layer(s), the flexural modulus of a multilayered balloon of the invention is expected generally to be about 90% to about 95% of the flexural modulus of a balloon consisting of the first (e.g., higher durometer) elastomeric polymeric material of the layer 30.

EXAMPLE

Multilayered balloon tubing, formed by coextrusion, had overall dimensions of 0.0155 inch inner diameter (ID) and 0.0365 inch outer diameter (OD). The tubing had an inner layer of 63 D PEBAX with a wall thickness 0.001 inches, a midlayer of 70 D PEBAX with a wall thickness of 0.001 inches, and an outer layer of 72 D PEBAX with a wall thickness of 0.0085 inches. Wall thickness values are a single wall thickness, unless otherwise identified as a double wall thickness (DWT). The tubing was blow-molded by heating and pressurizing the tubing in a 0.1215 inch ID balloon mold in a single blow cycle, resulting in a multilayered balloon having an average wall thickness (DWT) of 0.00163 inches and the following BURs for the balloon layers: 63 D Inner Layer ID of 0.0155 inch gives a BUR of 7.83 (0.1215/0.0155); 70 D midlayer ID of 0.0175 inch gives a BUR of 6.94 (0.1215/0.0175); and 72 D outer layer ID of 0.0195 inch gives a BUR of 6.23 (0.1215/0.0195). The calculated BUR value of balloons may vary slightly depending on whether the ID of the mold or the OD of the balloon at blow is used for the calculation. The resulting multilayered balloon had overall dimensions of about 0.1214 inch ID and 0.1230 inch OD.

The compliance and modulus of the multilayered balloon were compared to a comparison balloon similarly formed and with approximately the same wall thickness but from a single layer (100%) of the 72 D PEBAX. The comparison balloon was blow-molded in a 0.1250 inch ID balloon mold, using balloon tubing extruded to a 0.0190 inch ID and a 0.0365 inch OD, to form a balloon having the desired wall thickness. The resulting balloon had an average wall thickness of 0.00165 inches and a BUR of 6.58 (0.1250/0.0190). The multilayered balloon of the invention and the comparison monolithic balloon each had a nominal pressure of about 8 atm, and a burst pressure of greater than 20 atm, and more specifically, an average rupture pressure of about 25 atm. The compliance curves of the multilayered balloon and the comparison monolithic balloon are shown in FIG. 6, and are generated by inflating a balloon subassembly and measuring the change in the balloon outer diameter in response to increasing inflation pressures.

Figure 6:
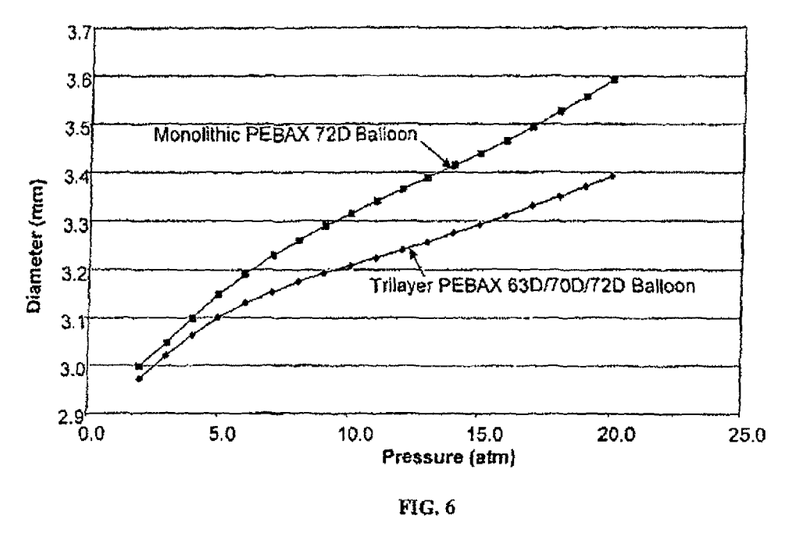
FIG. 6 is graphical compliance data, with balloon diameter measured in millimeters as the ordinate and inflation pressure measured in atmospheres as the abscissa, comparing a multilayered balloon of the invention with a single layered balloon formed of 100% of the highest durometer material.
Figure 7:
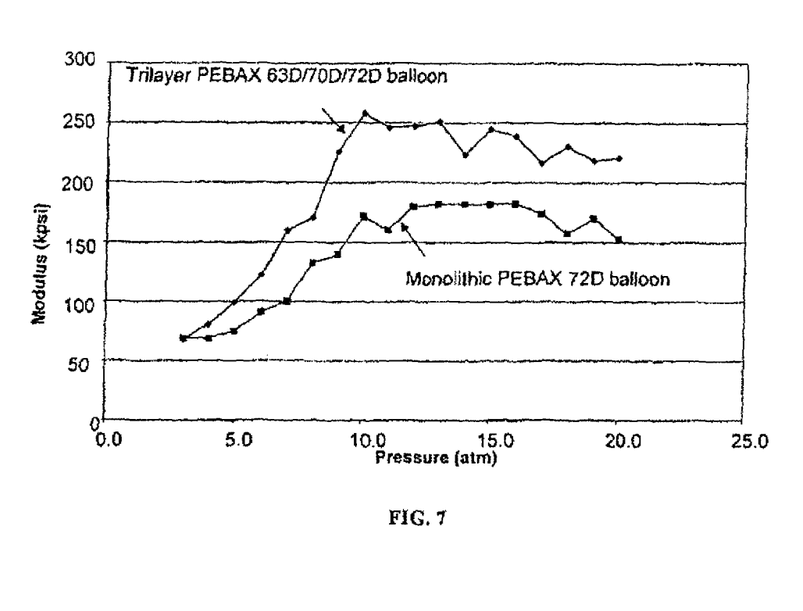
FIG. 7 is graphical modulus data, with balloon modulus in kpsi as the ordinate and inflation pressure measured in atmospheres as the abscissa, comparing a multilayered balloon of the invention with a single layered balloon formed of 100% of the highest durometer material.

As illustrated in FIG. 6, the compliance from nominal (8 atm) to 20 atm is about 0.018 mm/atm for the multilayered balloon of the invention, compared to about 0.028 mm/atm for the monolithic comparison balloon. Thus, despite the presence of the lower durometer material mid and inner layers, such that the 72 D PEBAX made up a smaller percentage of the wall thickness of the balloon than in the monolithic balloon made solely of 72 D PEBAX, the multilayered balloon of the invention had a lower compliance. Specifically, the outer layer of PEBAX 72 D made up about 87% of the wall thickness of the multilayered balloon, compared to 100% of the monolithic balloon. Similarly, FIG. 7 illustrates the incremental modulus comparison (modulus value from $P_n$ to $P_{n+1}$) of a trilayered Pebax 63 D/70 D/72 D balloon of the invention and a monolithic Pebax 72 D comparison balloon. The modulus of the multilayered balloon of the invention, illustrated graphically in FIG. 7, is higher than the modulus of the monolithic comparison balloon. The modulus values are derived from the compliance curve data, and are specifically determined from the equation $$E=((P_{n+1}D_{n+1})/DWT_{n+1}-(P_nD_n)/DWT_n)/(D_{n+1}-D_n)/D_n$$

where E is modulus, P is inflation pressure, D is diameter, and DWT is double wall thickness.

The BUR of the 72 D PEBAX outer layer of the trilayer balloon of the invention is less than the BUR of the monolithic 72 D PEBAX balloon. However, the multilayered balloon of the invention facilitates expanding the lower durometer inner layers to relatively high BURs, and provides a balloon with an overall BUR that is relatively high. The inner and mid layers are at relatively high BURs of about 7 to about 8, and preferably are at higher BURs than are possible if attempting to use the same blow-molding procedure to form a similar balloon but from 100% of the material of either the inner or the mid layer. For example, PEBAX 63 D extruded to form tubing having an ID of 0.0195 inches and an OD of 0.0355 inches can not be blown into a 0.118 inch ID balloon mold (i.e., a BUR of 6) in a single blow cycle without rupturing during the blow-molding process.

The absolute average wall thickness of the multilayered balloon in the above Example was about equal to the wall thickness of the monolithic balloon, allowing for a direct comparison of the compliance and modulus of the balloons. However, it should be understood that the wall thickness of the multilayered balloon of the invention could alternatively have been made less, so that the compliance and modulus comparisons would have been based on normalized wall thicknesses.

The dimensions of catheter 10 are determined largely by the size of the balloon and guidewire to be employed, the catheter type, and the size of the artery or other body lumen through which the catheter must pass or the size of the stent being delivered. Typically, the outer tubular member 19 has an outer diameter of about 0.025 to about 0.04 inch (0.064 to 0.10 cm), usually about 0.037 inch (0.094 cm), and the wall thickness of the outer tubular member 19 can vary from about 0.002 to about 0.008 inch (0.0051 to 0.02 cm), typically about 0.003 to 0.005 inch (0.0076 to 0.013 cm). The inner tubular member 20 typically has an inner diameter of about 0.01 to about 0.018 inch (0.025 to 0.046 cm), usually about 0.016 inch (0.04 cm), and a wall thickness of about 0.004 to about 0.008 inch (0.01 to 0.02 cm). The overall length of the catheter 10 may range from about 100 to about 150 cm, and is typically about 143 cm. Preferably, balloon 14 has a length about 0.8 cm to about 6 cm, and an inflated working diameter of about 2 to about 5 mm.

The various components may be joined using conventional bonding methods such as by fusion bonding or use of adhesives. Although the shaft is illustrated as having an inner and outer tubular member, a variety of suitable shaft configurations may be used including a dual lumen extruded shaft having a side-by-side lumens extruded therein. Similarly, although the embodiment illustrated in FIG. 1 is an over-the-wire type stent delivery balloon catheter, the catheter of this invention may comprise a variety of intravascular catheters, such as a rapid exchange type balloon catheter. Rapid exchange catheters generally comprise a shaft having a relatively short guidewire lumen extending from a guidewire distal port at the catheter distal end to a guidewire proximal port spaced a relatively short distance from the distal end of the catheter and a relatively large distance from the proximal end of the catheter.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

The invention claimed is:

1. A method of making a multilayer balloon for a catheter comprising:
   selecting a first polymeric material having a first maximum blow-up-ratio;
   selecting a second polymeric material having a second maximum blow-up-ratio greater than the first maximum blow-up-ratio; and
   forming a multilayer balloon having at least a first layer of the first polymeric material and a second layer of the second polymeric material having a combined wall thickness, wherein the second layer is an inner layer relative to the first layer, and wherein the at least first and second layers define a compliance less than that of a single layer balloon made of the first polymer material with a wall thickness equal to the combined wall thickness.

2. The method of claim 1, wherein forming the multilayer balloon includes blow-molding the at least first layer and second layer by radial expansion in a balloon mold having an inner diameter.

3. The method of claim 2, wherein the inner diameter is selected so that at least the second layer is substantially at the second maximum blow-up-ratio when the multilayer balloon is substantially at a nominal working diameter corresponding to the inner diameter of the balloon mold.

4. The method of claim 3, wherein the first layer is substantially at the first maximum blow-up-ratio when the multilayer balloon is substantially at the nominal working diameter.

5. The method of claim 2, wherein the forming the multilayer balloon includes longitudinally stretching the at least first and second layers.

6. The method of claim 5, wherein the at least first and second layers are longitudinally stretched about 200%.

7. The method of claim 5, wherein the multilayer balloon is biaxially oriented.

8. The method of claim 1, wherein the second maximum blow-up-ratio is about 15 to about 40 percent greater than the first maximum blow-up-ratio.

9. The method of claim 1, wherein the first maximum blow-up-ratio is about 6 to about 7.

10. The method of claim 1, wherein the second maximum blow-up-ratio is about 7 to about 8.

11. The method of claim 1, wherein the second layer has a thickness of about 5 to about 15 percent of the combined wall thickness.

12. The method of claim 1, wherein the first layer has a first Shore durometer hardness and the second layer has a second Shore durometer hardness lower than the first Shore durometer hardness.

13. The method of claim 12, wherein the first Shore durometer hardness is about 70 D to about 72 D.

14. The method of claim 12, wherein the second Shore durometer hardness is about 60 D to about 70 D.

15. The method of claim 1, wherein the balloon has a higher modulus than a single layer balloon made of the first polymer material with a wall thickness equal to the combined wall thickness.

16. The method of claim 1, wherein the second layer defines an inner surface of the balloon.

17. The method of claim 16, wherein the first layer defines an outer surface of the balloon.

18. The method of claim 17, wherein the at least first and second layers further include a mid layer between the first layer and the second layer.

19. The method of claim 18, wherein the mid layer is a tie layer.

20. The method of claim 18, wherein the mid layer has a maximum blow-up-ratio greater than the first maximum blow-up-ratio and less than the second maximum blow-up-ratio.

21. The method of claim 18, wherein the first layer has a first Shore durometer hardness, the second layer has a second Shore durometer hardness lower than the first Shore durometer hardness, and the mid layer has a third Shore durometer hardness lower than the first Shore durometer hardness and greater than the second Shore durometer hardness.

22. The method of claim 21, wherein the first Shore durometer hardness is about 70 D to about 72 D and the second Shore durometer hardness is about 60 D to about 70 D.

23. The method of claim 18, wherein the second layer and the mid layer collectively have a total thickness of about 5 to about 15 percent of the combined wall thickness of the first, second, and mid layers.

24. The method of claim 1, wherein the first polymer material is a polyamide, a polyurethane, a polyester, or polyether block amide.

25. The method of claim 1, wherein the second polymer material is a polyamide, a polyurethane, a polyester, or polyether block amide.

26. The method of claim 1, wherein the first polymer material is a polyether block amide and the second polymer material is a polyether block amide.

27. The method of claim 26, wherein the first polymer material has a Shore durometer hardness of about 70 D to about 72 D and the second polymer material has a Shore durometer hardness of about 63 D.

28. The method of claim 1, wherein the first layer has a first elongation and the second layer has a second elongation about 10 to about 50 percent more than the elongation of the first layer.

29. The method of claim 1, wherein the at least first and second layers collectively define a rated burst pressure of about 14 to about 22 atm.

30. The method of claim 29, wherein the rated burst pressure is about 18 to about 20 atm.

31. The method of claim 1, wherein the at least first and second layers collectively define a burst pressure greater than a single layer balloon made of the first polymer material having a wall thickness equal to the combined wall thickness.

32. The method of claim 1, wherein the first layer is bonded directly to the second layer.

33. The method of claim 1, further comprising mounting an expandable stent on an outer surface of the multilayer balloon.

34. The method of claim 1, wherein the multilayer balloon has a rupture pressure generally equal to or greater than that of a single layer balloon made of the first polymer material having a wall thickness equal to the combined wall thickness.

35. The method of claim 1, wherein the multilayer balloon is generally noncompliant with a compliance of less than about 0.03 mm/atm between nominal pressure and a rated burst pressure.

36. The method of claim 35, wherein the multilayer balloon compliance from nominal pressure to a rated burst pressure is less than about 0.018 mm/atm.

* * * * *